United States Patent
Ohtsuka et al.

(10) Patent No.: US 9,442,154 B2
(45) Date of Patent: Sep. 13, 2016

(54) NON-CONTACT DISCHARGE EVALUATION METHOD AND NON-CONTACT DISCHARGE EVALUATION APPARATUS

(71) Applicant: KYUSHU INSTITUTE OF TECHNOLOGY, Fukuoka (JP)

(72) Inventors: Shinya Ohtsuka, Fukuoka (JP); Masaaki Furukawa, Fukuoka (JP); Yuki Yamaguchi, Fukuoka (JP)

(73) Assignee: KYUSHU INSTITUTE OF TECHNOLOGY, Kitakyushu-shi, Fukuoka (JP)

( * ) Notice: Subject to any disclaimer, the term of this patent is extended or adjusted under 35 U.S.C. 154(b) by 88 days.

(21) Appl. No.: 14/374,424

(22) PCT Filed: Nov. 29, 2012

(86) PCT No.: PCT/JP2012/080816
§ 371 (c)(1),
(2) Date: Jul. 24, 2014

(87) PCT Pub. No.: WO2013/111445
PCT Pub. Date: Aug. 1, 2013

(65) Prior Publication Data
US 2014/0361789 A1  Dec. 11, 2014

(30) Foreign Application Priority Data

Jan. 25, 2012 (JP) ................................. 2012-013305

(51) Int. Cl.
G01R 31/12 (2006.01)
G01N 21/67 (2006.01)
H01T 13/60 (2011.01)

(52) U.S. Cl.
CPC ........... *G01R 31/1218* (2013.01); *G01N 21/67* (2013.01); *G01N 2201/08* (2013.01); *H01T 13/60* (2013.01)

(58) Field of Classification Search
CPC .... G01N 21/68; G01N 21/67; G01N 21/645;
G01N 2021/4742; H01J 37/32174; H01J 37/32935; H01J 37/224; B41J 11/002; B41M 7/0081; F21Y 2101/02; G09G 2320/0233; G09G 3/3291; G09G 2310/066
See application file for complete search history.

(56) References Cited

U.S. PATENT DOCUMENTS

2009/0015814 A1* 1/2009 Mueller ............. G03F 7/70558
355/68

FOREIGN PATENT DOCUMENTS

| JP | 2707823 B2 | 2/1998 |
| JP | 2008-268083 A | 11/2008 |
| JP | 2008-304357 A | 12/2008 |
| JP | 2010-101671 A1 | 5/2010 |

(Continued)

OTHER PUBLICATIONS

Bendjamin J et al., Remote Sensing of ESD through Optical and Magnetic Radiation Fields, IEEE Transactions on Dielectrics and Electrical Insulation, Dec. 1999, vol. 6, No. 6, pp. 896-899.*

(Continued)

*Primary Examiner* — Arleen M Vazquez
*Assistant Examiner* — Alesa Allgood
(74) *Attorney, Agent, or Firm* — McGlew and Tuttle, P.C.

(57) ABSTRACT

The magnitude (charge quantity) and energy of discharge are obtained by optical measurement based on light emission, and are evaluated. A discharge source is caused to emit discharge light by applying a voltage to the discharge source from a known power supply, the intensity waveform of the discharge light emission is measured using a light receiving element, the waveform of discharge current is simultaneously measured using a current conversion probe or a current waveform detector, and a database is created in which a relation with analysis data sets obtained by analyzing the waveforms is recorded in consideration of applied power information. The intensity waveform of discharge light emission from a piece of equipment under measurement is measured using the light receiving element, and light emission data obtained by analyzing the waveform is compared with the data recorded in the database so as to estimate the magnitude of discharge as a value.

13 Claims, 8 Drawing Sheets

(56) References Cited

FOREIGN PATENT DOCUMENTS

JP 2010-204067 A 9/2010
JP 2011-99775 A 5/2011

OTHER PUBLICATIONS

Ryuichi Ishino, "Hoden Bubun no Hakko Menseki o Mochiita More Denryu Suitei Shuho no Kaihatsu (sono 2)—Shiryohen no Sokutei Kekka ni Motozuku Haiden'yo Kobunshi Gaishi no More Denryu Suitei-", Central Research Institute of Electric Power Industry, System Engineer Research Laboratory Kenkyu Hokoku, No. R05008, May 2006.

R. Ishino et al., "Leakage current Estimation Using Luminance Area of Discharge in Ultra Violet Image (No. 1)", Research report from Central Research Institute of Electric Power Industry, Rep. No. R04013, Jun. 2005.

* cited by examiner

FIG. 4 ( A )
RELATION BETWEEN DISCHARGE LIGHT EMISSION
INTENSITY AND DISCHARGE CURRENT
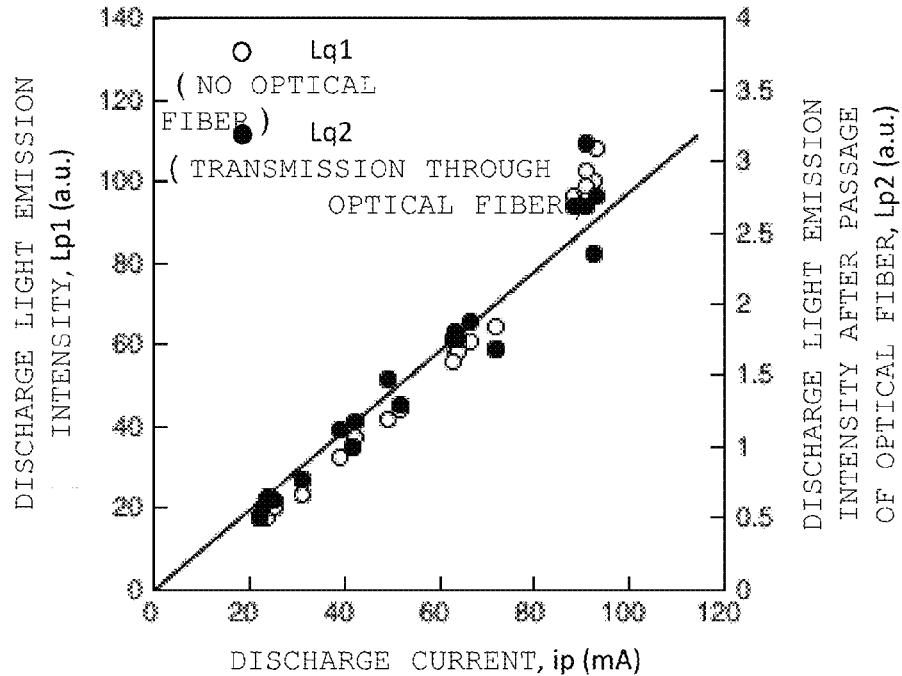
FIG. 4 ( B )
RELATION BETWEEN DISCHARGE LIGHT EMISSION
INTEGRAL VALUE AND DISCHARGE CHARGE QUANTITY
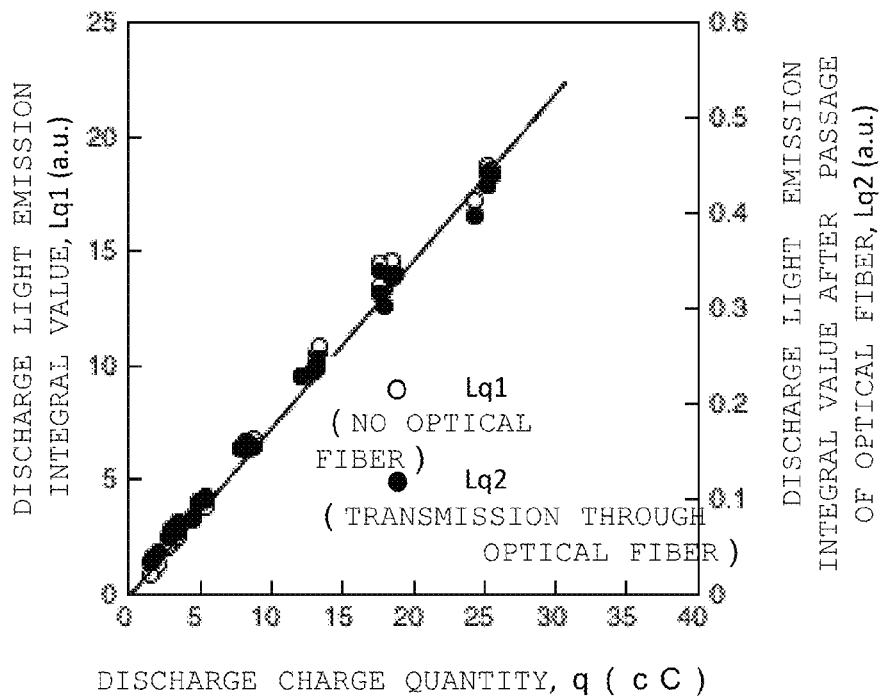

NON-CONTACT DISCHARGE EVALUATION METHOD AND NON-CONTACT DISCHARGE EVALUATION APPARATUS

This application claims the benefit of PCT International Application Number PCT/JP2012/080816 filed Nov. 29, 2012 and Japanese Application No. 2012-013305 filed, Jan. 25, 2012 in Japan, the disclosures of which are incorporated herein by reference.

TECHNICAL FIELD

The present invention relates to a method and an apparatus for evaluating discharge of equipment under measurement in a non-contact manner by optically measuring light emitted as a result of the discharge. The present invention can be used in the fields of high voltage and electrical insulation in power and electric equipment, the fields of electrostatic discharge tests of electric and electronic equipment or the like, and the fields of manufacture and maintenance/operation of automobiles or electric energy equipment.

BACKGROUND ART

In order to detect and evaluate an anomaly of electrical insulation, there has been performed detection and evaluation of partial discharge, which is a phenomenon occurring before occurrence of dielectric breakdown. A partial discharge test has been prescribed as an insulation test for high voltage equipment. In general, the magnitude of discharge is evaluated by charge quantity (unit: coulomb C). Conventionally, such charge quantity has been measured by measuring discharge current and converting it into charge quantity, or by connecting a charge quantity evaluation apparatus to a circuit. In an electrostatic discharge test, since the rising time of the voltage generated by an electrostatic discharge tester (ESD gun) is 1 ns or less (i.e., the rising is steep), it is difficult to electrically measure generation of discharge near the tester.

Evaluating the magnitude (charge quantity) and energy of discharge in a non-contact manner has been demanded at a site where high-voltage power equipment or electrically driven or controlled electric energy equipment are manufactured, or in the field of maintaining and operating such equipment. A technique of measuring discharge current in a non-contact manner has drawn attention in view of safety, easiness of tests, and expected expansion of application fields. A UHF method of detecting radiation electromagnetic waves of discharge (measuring radiation electromagnetic waves in the UHF band (300 MHz to 3 GHz)) has drawn attention, and establishment of a standard for the UHF method as an IEC standard is in progress.

Meanwhile, measurement of electromagnetic waves has a problem in that electrical measurement becomes difficult if an environment is bad in term of electromagnetic noise. In particular, in a lightning impulse test and an electrostatic discharge test, strong electromagnetic waves serving as noise are radiated from their power supplies, and measurement is performed in a poor environment in terms of electromagnetic noise.

Also, there has been conventionally known an apparatus of measuring the number of times of generation of partial discharge in which partially discharge is judged and detected through use a photomultiplier tube which detects light emission in a container (see Patent Document 1). Further, there has been known a failure monitoring apparatus which monitors failures of electric equipment by detecting light emitted as a result of flashover or partial discharge occurring at a high-voltage portion of the electric equipment (Patent Document 2). The apparatus disclosed in Patent Document 2 judges that light emission has occurred in a container and a failure has occurred when the intensity of the detected light converted to an electric signal exceeds a predetermined level.

However, the relation between light and discharge energy is unclear. There has been demand for a technique which not only detects the number of times of generation of discharge or light emission itself, but also evaluates the magnitude and energy of discharge through optical measurement.

PRIOR ART DOCUMENTS

Patent Documents

Patent Document 1: Japanese Patent Application Laid-Open (kokai) No. 2010-204067
Patent Document 2: Japanese Patent No. 2707823

SUMMARY OF THE INVENTION

Problems to be Solved by the Invention

In view of the above-described circumstances, an object of the present invention is to obtain the magnitude (charge quantity and current peak value) and energy of discharge, for the purpose of evaluation, through optical measurement based on light emission, rather than electrically obtaining these quantities.

Means for Solving the Problems

A non-contact discharge evaluation method and a non-contact discharge evaluation based on the present invention evaluate discharge of a piece of equipment under measurement in a non-contact manner by optically measuring light emitted as a result of the discharge. In the method and apparatus, a database is created as follows. A voltage is applied to a discharge source from a known power supply so as to cause the discharge source to emit discharge light, the intensity waveform of the discharge light emission is measured using a light receiving element, the waveform of discharge current is simultaneously measured using a current conversion probe or a current waveform detector, the waveforms are analyzed to obtain analysis data sets, the relation with the analysis data sets is recorded in the database in consideration of applied power information such as the voltage applied to the discharge source and the polarity of the applied voltage or the voltage instantaneous value and its generation time (phase) when discharge is generated. The apparatus includes a waveform intensity obtaining apparatus which measures an intensity waveform of discharge light emission from the piece of equipment under measurement by using a light receiving element which is identical to or of the same type as the light receiving element and obtains a waveform intensity thereof; a waveform analyzing section which analyzes the waveform intensity obtained by the waveform intensity obtaining apparatus; a comparison section which compares light emission data obtained by analysis in the waveform analyzing section with the data recorded in the database so as to estimate the magnitude of discharge as a value; and a display section which displays the estimated magnitude of discharge.

The database is created and the magnitude of discharge is estimated for each light receiving element used and for a discharge environment produced in each insulation system of interest such as an insulation gas such as SF6 gas or air (including vacuum) or an insulation liquid such as insulation oil or silicone oil. The magnitude of discharge is the peak value of discharge current, the charge quantity of discharge which is the integral value of the discharge current, or the discharge energy value. The magnitude of discharge is evaluated on the basis of the peak value or area (integral value) of the measured discharge light emission intensity waveform.

The light receiving element is disposed to spatially face the discharge source or is disposed such that the light receiving element is coupled with the discharge source through an optical guide. The sensitivity of the light receiving element is increased and decreased in accordance with the light emission intensity by increasing and decreasing the gain of the light receiving element itself or increasing and decreasing the distance between the light receiving element and the light emission source, or the sensitivity of the light receiving element is adjusted by disposing an optical filter or using an optical guide. The light receiving element and the waveform intensity obtaining apparatus may be disposed in an electromagnetic shield box. A plurality of light receiving elements may be used. In this case, the wiring distances between the light receiving elements and the waveform intensity obtaining apparatus are made equal to one another, or time correction is performed in accordance with length differences thereamong.

Effect of the Invention

According to the present invention, the magnitude (charge quantity and current peak) and energy of discharge can be obtained for evaluation in a non-contact manner through optical measurement based on light emission even in a place whose electromagnetic noise environment is poor.

BRIEF DESCRIPTION OF DRAWINGS

FIGS. 4(A) and 4(B) are graphs showing an example of a characteristic when an optical guide (optical fiber) is used.

MODE FOR CARRYING OUT THE INVENTION

Figure 1:
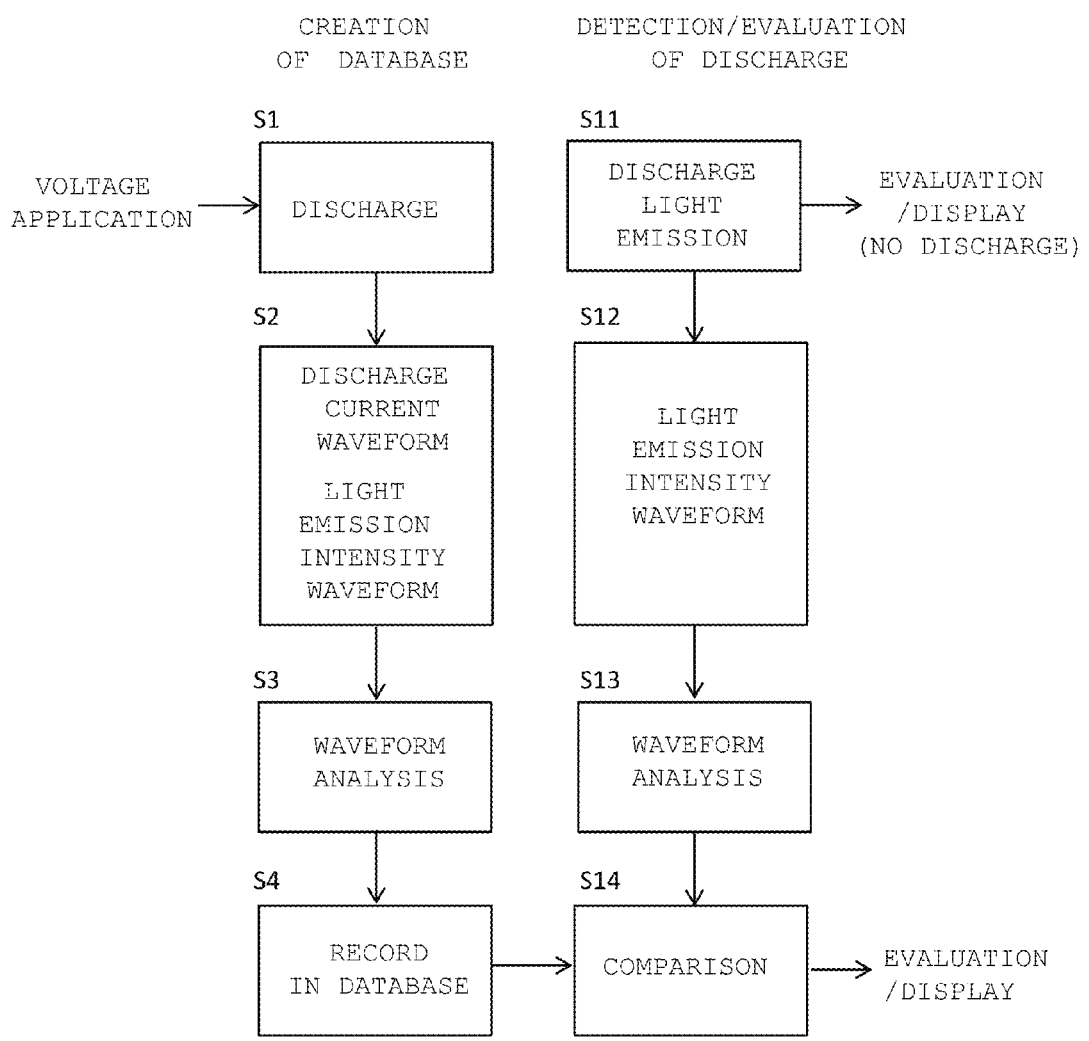
FIG. 1 is an operational diagram exemplifying a non-contact discharge evaluation method according to the present invention.

The present invention will now be described by way of examples. FIG. 1 is an operational diagram exemplifying a non-contact discharge evaluation method according to the present invention. In the present invention, for each light receiving element used in a corresponding insulation system environment of interest (e.g., a space filled with an insulating gas used), a database showing the correlation between light signal (at least the peak value Lp of a light intensity waveform or the area Lq of the light intensity waveform) and the magnitude of discharge (the charge quantity q of discharge, the peak value ip of discharge current, the energy E of discharge) is created in consideration of applied power information (at least applied voltage, polarity, instantaneous voltage and its generation time (or phase) when light is emitted due to discharge (hereinafter referred to as "discharge light emission"). When discharge on a piece of equipment under measurement used in a different insulation system is evaluated and the magnitude of the discharge is estimated, data recorded in this database are used.

First, in order to create a database, in step S1, a voltage is applied to a discharge source for test from a power supply whose information (power supply information) is known. As a result, discharge light emission occurs. In step S2, the intensity waveform of the discharge light emission is measured using a light receiving element. At the same time, the waveform of discharge current is measured using a current conversion probe CT, a current waveform detector, or the like which has frequency response up to several GHz. In step S3, these waveforms are analyzed to obtain analysis data sets. In step S4, for each light receiving element to be used and for each discharge environment of interest, the relation between the peak value Lp of the light intensity waveform and the area (integral value) Lq of the light intensity waveform and the magnitude of discharge (the peak value ip of discharge current, the charge quantity q of discharge, the energy E of discharge) is obtained from the analysis data sets in consideration of applied power information. The obtained relation is recorded in the database. This is because the waveform of discharge current and the light emission intensity waveform differ among discharge environments.

Next, through use of the data recorded in the database, the magnitude of discharge (current peak, charge quantity of discharge, and discharge energy) are evaluated on the basis of data of the measured light emission, and their values are estimated. In step S11, discharge light emission from a piece of equipment under measurement is detected. In the case where discharge did not occur, no evaluation is made, and the fact that discharge did not occur is displayed. The present invention can be used in discharge tests for power equipment, electric/electronic equipment, or electric energy equipment such as electric vehicles or aircrafts which are electrically driven or controlled. The present invention can also be used for monitoring of electrical insulation anomalies. In steps S12 and S13, the intensity waveform of discharge light emission is measured using a light receiving element which is identical to or is of the same type as the light receiving element used for creation of the database, and the waveform is analyzed. In step S14, the light emission data obtained through this analysis are compared with the data recorded in the database so as to estimate the peak value ip of discharge current, the charge quantity q which is the integral value of discharge current, and the value of discharge energy E.

Figure 2:
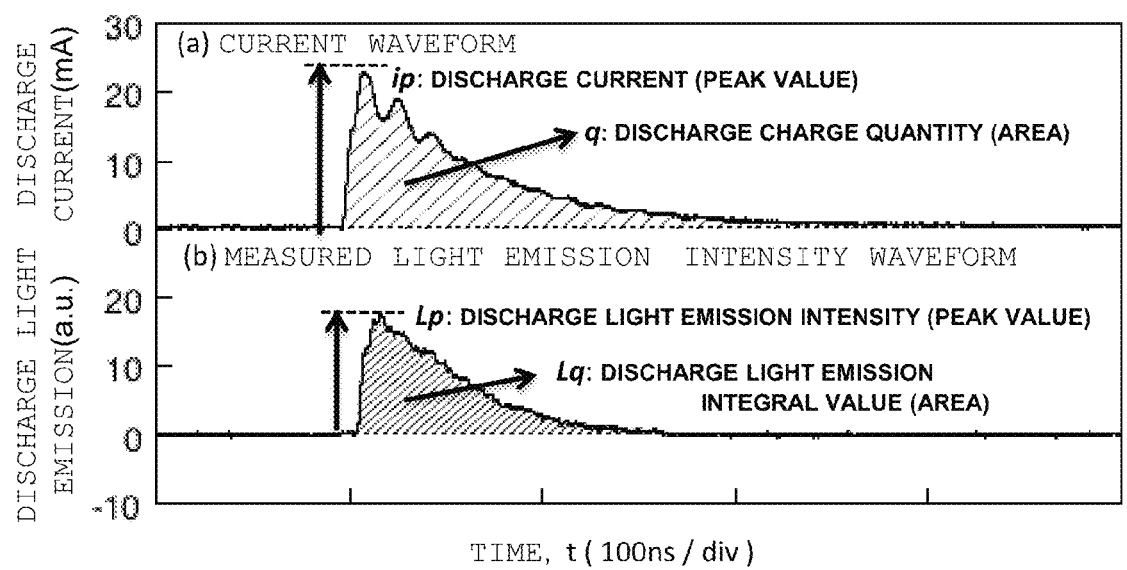
FIG. 2 is a graph used for explaining the definition of waves.

FIG. 2 is a graph used for explaining the definition of waves. The horizontal axis shows time. The waveform of discharge current is shown on the upper side of the graph, and the intensity waveform of discharge light emission measured simultaneously is shown on the lower side of the graph. In the present invention, through use of the data recorded in the database, discharge current is evaluated on the basis of the intensity of the measured discharge light emission. Specifically, the peak value ip of discharge current is evaluated on the basis of the peak value Lp of the light intensity waveform. Alternatively, the peak value ip of discharge current may be evaluated on the basis of the area Lq of light intensity waveform. Also, the charge quantity q which is the integral value of the discharge current is evaluated on the basis of the area (integral value) Lq of the light intensity waveform. Alternatively, the charge quantity q may be evaluated on the basis of the light intensity peak Lp. Also, the discharge energy E is evaluated on the basis of the area (integral value) Lq of the light intensity waveform or the light intensity peak Lp. The details of the evaluation will be described later.

Figure 3:
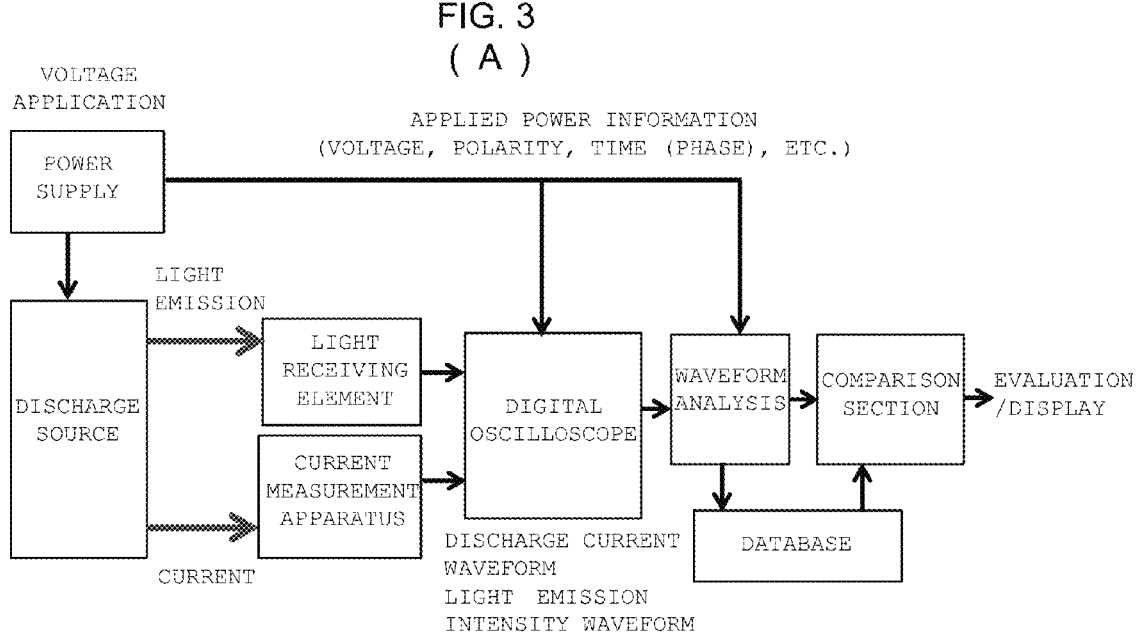
FIGS. 3(A) and 3(B) are circuit diagrams exemplifying non-contact discharge evaluation apparatuses which differ from each other.
Figure 3:
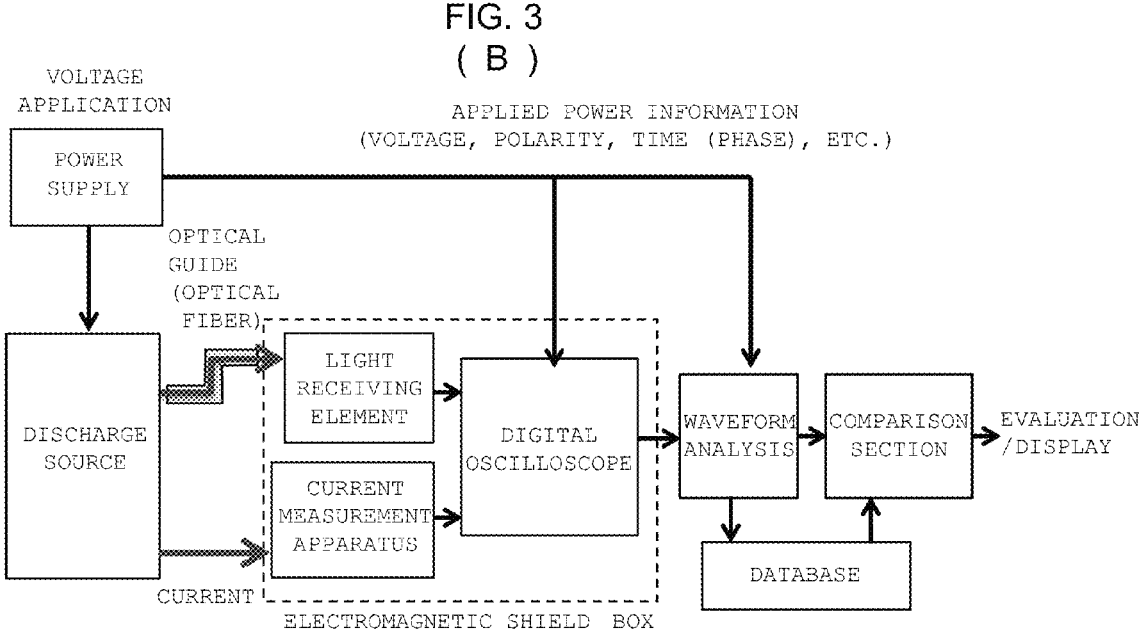

FIGS. 3(A) and 3(B) are circuit diagrams exemplifying non-contact discharge evaluation apparatuses which differ from each other. The circuit diagram shown in FIG. 3(B) differs from the circuit diagram shown in FIG. 3(A) only in the point that the light receiving element is connected through an optical guide and the point that a light receiving element, a current measurement apparatus, and a digital oscilloscope are disposed in an electromagnetic shield box.

As described above, when a database is created, a voltage is applied to a discharge source for test from a power supply whose information is known. The power supply voltage may be the output voltage of an ESD gun (in the case of an electrostatic discharge test) or a lightening impulse voltage (in the case of a lightening impulse test). Alternatively, the power supply voltage may be an AC or DC test voltage. In either case, the applied voltage, the polarity of the applied voltage, and the instantaneous voltage and it generation time (or phase) at the time of generation of discharge are known. The discharge current is measured by a current measuring apparatus. However, at the time of a discharge test or maintenance/operation performed after creation of the database, discharge current is not measured, and only the measurement of the light emission intensity waveform by the light receiving element is performed.

When a database is created or when discharge of a piece of equipment under measurement is evaluated, light emission is detected using the same light receiving element or a light receiving element of the same type (i.e., having the same characteristic). The optical signal input to each light receiving element is weakened or its sensitivity is increased. The sensitivity is increased or decreased in accordance with the light emission intensity by increasing or decreasing the distance between the light receiving element and the light emission source, disposing an optical filter, using an optical guide such as optical fiber, or adjusting the gain of the light receiving element. An example of a light receiving element having high sensitivity from the range of UV light to the range of visible light is a photomultiplier tube PMT. In the case where the light emission intensity is high, a photo diode may be used instead of the photomultiplier tube PMT. In the case where the light emission intensity is higher, a light-weakening filter is used.

As shown in FIG. 3(A), the light receiving element is disposed to spatially face the discharge source so as to detect generation of discharge. Alternatively, as shown in FIG. 3(B), the light receiving element may be coupled with the discharge source through an optical guide such as optical fiber. In this case, the positional relation between the discharge source and the light receiving element can be set such that they are not located on a common straight line, and they can be separated from each other. This configuration can suppress the influence, on the light receiving element, of electrical noise from the power supply or the discharge source.

In the case where a strong noise source exists and noise is induced in a light receiving element to be used, the light receiving element is separated from a portion where discharge light is emitted, and a light emission signal is transmitted therebetween through an optical fiber cable. In this case, the light emission signal attenuates. Therefore, evaluation is performed in consideration of attenuation of the light emission intensity at the optical fiber cable. Notably, an optical fiber may also be used when the quantity of light is large (the light intensity drops as a result of passage through the fiber). Use of an optical guide such as optical fiber not only reduces electrical noise but also allows flexible determination of the positions of a portion where light emission occurs (light source) and the light receiving element.

FIGS. 4(A) and 4(B) are graphs showing an example of a characteristic when an optical guide (optical fiber) is used. FIG. 4(A) shows the relation between the intensity of discharge light emission and discharge current, and FIG. 4(B) shows the relation between the integral value of discharge light emission and the charge quantity of discharge. In the case where an optical fiber (a bundle of quarts fibers) is used, since the light emission intensity decreases, as shown in FIG. 4(A), the intensity Lp of discharge light emission is smaller. However, the intensity Lp of discharge light emission and the peak value ip of discharge current have a linear relationship in both the case where an optical fiber is used and the case where no optical fiber is used. Similarly, as shown in FIG. 4(B), the integral value Lq of discharge light emission and the charge quantity q of discharge have a linear relationship in both the case where an optical fiber is used and the case where no optical fiber is used. When an optical fiber is used, the characteristic obtained when the optical fiber is used is normalized to the characteristic obtained when the optical fiber is not used such that the two characteristics become the same.

Further, when the light receiving element and the digital oscilloscope are disposed in an electromagnetic shield box as shown in FIG. 3(B), the influence of electrical noise can be suppressed further. For example, in the case where no optical guide is provided, a light emitting portion and the light receiving element must be located on a straight line within the angular field of view of the light receiving element. However, use of an optical guide removes the restriction (the light receiving element must be located on a straight line within the angular field of view), and allows the light receiving element to be disposed freely disposed, for example, behind a shield or within an electromagnetic shield box disposed at an arbitrary position. Notably, in order to suppress electrical noise input to the light receiving element to a greater degree, it is effective that a metal mesh which does not allow passage of electrical noise therethrough but allows passage of optical signals therethrough is disposed as an electromagnetic shield box covering the entire surface of the light receiving element. Also, it is desired that the current measuring apparatus be disposed in the electromagnetic shield box.

In the above, there has been described the case where a single light receiving element is provided. However, a plurality of light receiving elements may be used. In this case, the wiring distances between the light receiving elements and a waveform intensity obtaining apparatus such as a digital oscilloscope DOSC are made equal to one another (in the case where the distances are not equal to one another, the times at which waveforms appear are corrected in accordance with length differences thereamong). Thus, in the case where discharge is generated at a plurality of locations or the timings at which discharge is generated differ from one another, the generation positions and differences between the generation times can be known more specifically by performing experimental observation one time. The optical guide such as optical fiber must have a diameter sufficient for observation of the size of discharge light emission. Notably, the optical guide may be a single thick optical fiber or a bundle of a plurality of optical fibers. The optical guide such as optical fiber is disposed at a position at which discharge light emission can be received efficiently. Therefore, light may be condensed through use of, for example, a lens which allows passage of light over the entire range of wavelengths of emitted light.

The light emission intensity waveform detected by the light receiving element is observed by the waveform obtaining apparatus such as a digital oscilloscope DOSC. In addition, data representing the light emission intensity waveform are obtained. The frequency band and sampling frequency of the oscilloscope must be sufficient to cope with changes in the light emission intensity waveform. For example, it is desired that the frequency band be equal to or higher than 500 MHz, and the sampling frequency be equal to or higher than 1 GS/s. The signal from the light receiving element itself is used as a trigger of the digital oscilloscope DOSC. However, in an electrostatic discharge test or a lightening impulse test, a single-short voltage or a single-short current is applied. Therefore, a drive signal of a tester used in such a test (for example, an ESD gun used in the electrostatic discharge test or a lightening impulse voltage or current generator used in the lightening impulse test) or its output application signal may be used as a trigger signal. An electromagnetic wave radiated from the drive signal or output application signal may be detected by an antenna and be used as a trigger signal. Furthermore, in an AC or DC test or the above-mentioned lightening impulse test, observation is performed within a predetermined time period or at a predetermined phase (in the case where an AC signal is used). In such a case, there may be used a delay circuit or a pulse generator which produces a trigger signal at the predetermined time or phase.

The light emission intensity waveform obtained by the waveform obtaining apparatus such as a digital oscilloscope DOSC is analyzed by a waveform analyzing section. When a database is created, for each light receiving element to be used and for the discharge environment of each insulation system of interest, the relation between the peak value Lp of the light intensity waveform or the area Lq of the light intensity waveform and the peak value ip of the discharge current value, the charge quantity q of discharge (the integral value of the discharge current waveform), or the discharge energy E is obtained from the analysis data sets in consideration of applied power information (applied voltage, polarity, instantaneous voltage and its generation time (or phase) when discharge is generated. The obtained relation is recorded in the database. At the time of discharge evaluation, in a comparison section, the light emission data obtained by the analysis are compared with the data recorded in the database so as to estimate the magnitude of discharge (current peak value, charge quantity of discharge, and discharge energy). The results of the estimation are displayed.

Figure 5:
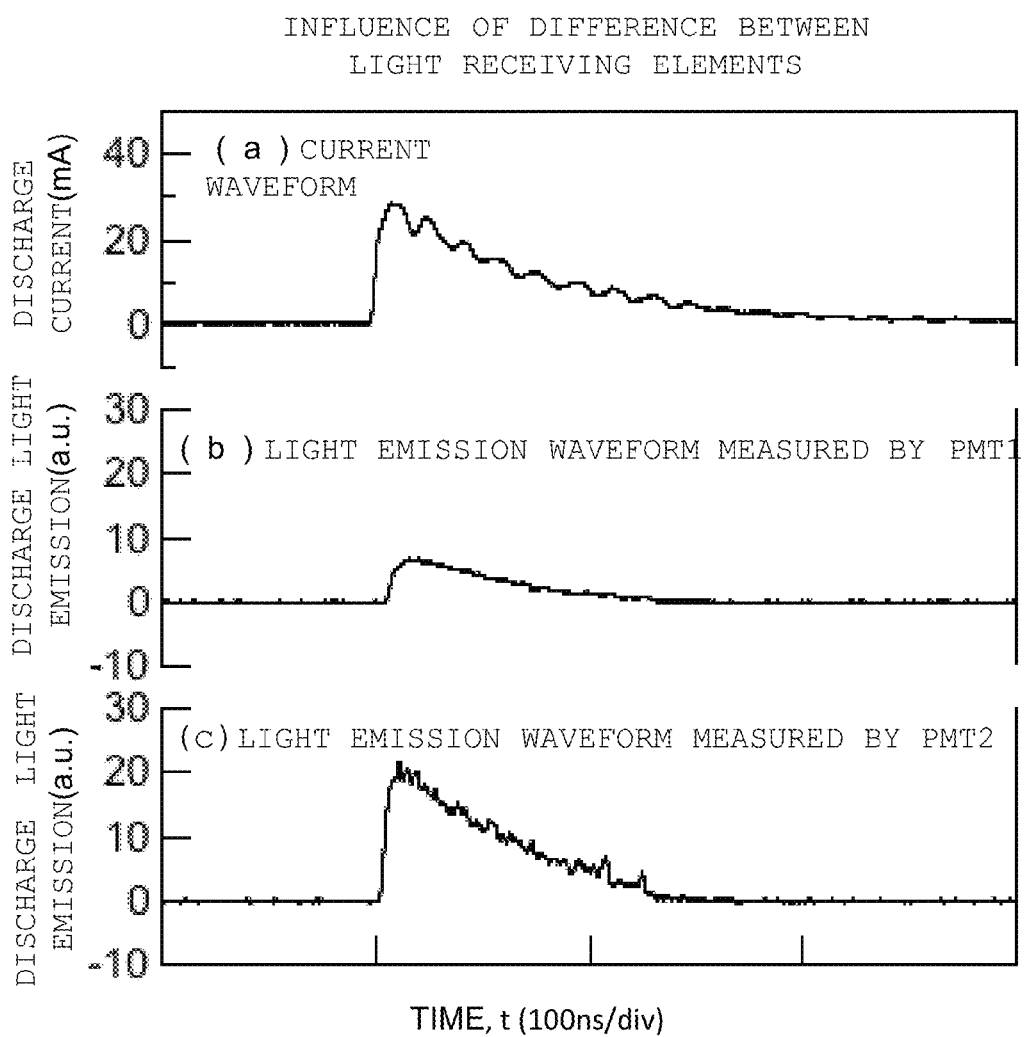
FIG. 5 is a graph showing an influence due to a difference between light receiving elements.

FIG. 5 is a graph showing an influence due to a difference between light receiving elements. FIG. 5 shows the results of an experiment in which the same discharge light emission was measured using different types of photomultiplier tubes PMT. Although the light emission intensity changes depending on the type of the element (photomultiplier tube PMT) used, the magnitude of discharge can be evaluated quantitatively by creating a database for each element to be used.

Figure 6:
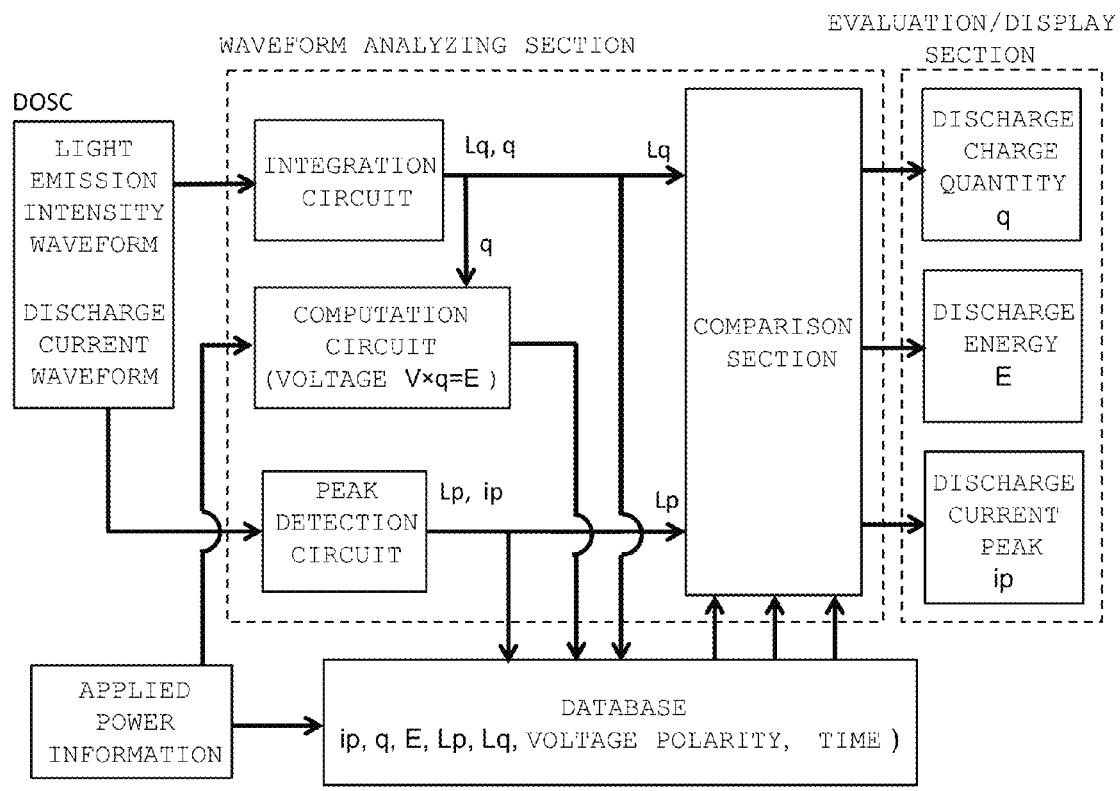
FIG. 6 is a detailed diagram of the waveform analysis, comparison, and evaluation shown in FIGS. 3(A) and 3(B).

FIG. 6 is a detailed diagram of the waveform analysis, comparison, and evaluation shown in FIGS. 3(A) and 3(B). Values representing the discharge light emission intensity waveform and the discharge current waveform are led from the digital oscilloscope DOSC to an integration circuit and a peak detection circuit of the waveform analyzing section. The integration circuit calculates the integral value Lq of the output waveform of the light receiving element and the integral value q of the output waveform of the current conversion probe CT or the current waveform detection apparatus. The peak detection circuit calculates the peak value Lp of the output waveform of the light receiving element and the peak value ip of the output waveform of the current conversion probe CT or the current waveform detection apparatus. Further, in a computation circuit, the discharge energy E is calculated by obtaining the product of the output q from the integration circuit and the voltage V at the time of emission of light (applied power information). In the present invention, the peak value ip of the discharge current waveform, the charge quantity q of discharge which is the area (time integral value) of the waveform, and the discharge energy E are evaluated on the basis of the peak value Lp and integral value Lq of the output waveform of the light receiving element. In particular, the peak value ip of the discharge current waveform is evaluated on the basis of the peak value Lp of the output waveform of the light receiving element, and the charge quantity q of discharge is evaluated on the basis of the integral value Lq of the output waveform of the light receiving element. The discharge energy E may be evaluated on the basis of the peak value Lp or the integral value Lq because a large difference is not produced between the two cases.

Figure 7:
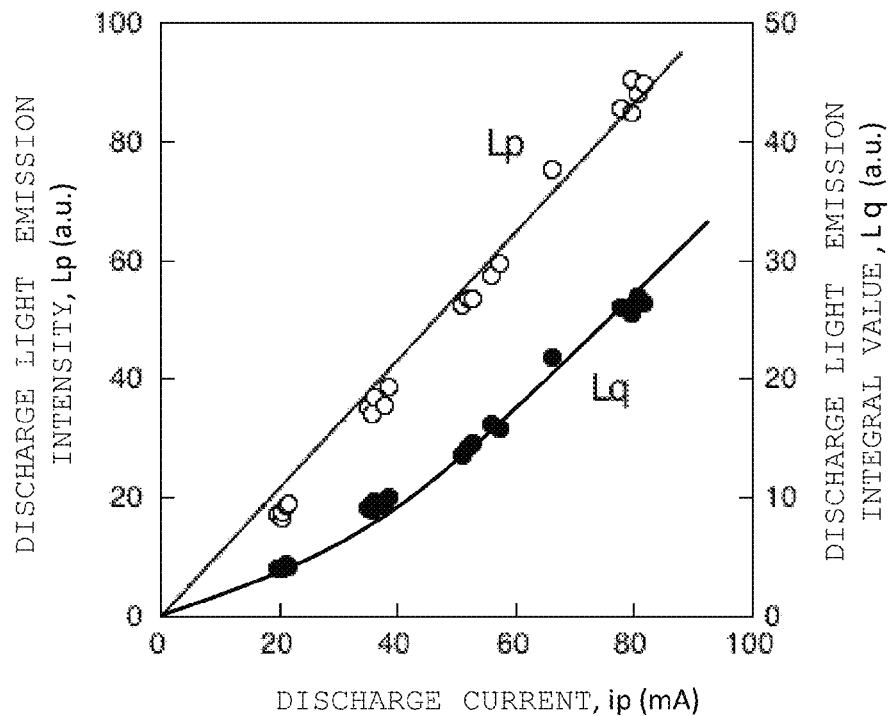
FIG. 7 is a graph used for explaining estimation of the peak value ip of discharge current, wherein plots show actually measured values, and lines show approximate characteristic curves corrected for creation of a database.

FIG. 7 is a graph used for explaining an operation of measuring a light emission signal, such as the peak value Lp of the light emission intensity waveform or the integral value Lq of the light emission intensity, simultaneously with the peak value of discharge current and estimating the peak ip of discharge current from Lp or Lq on the characteristic curves shown in FIG. 7. In FIG. 7, plots show actually measured values, and lines show approximate characteristic curves corrected for creation of a database. The points on the characteristic curves of this graph are recorded in the database in the form of a table. The relation between the peak value ip of the discharge current waveform and the peak value Lp of the output waveform is more linear than the relation between the peak value ip of the discharge current waveform and the integral value Lq. Moreover, from the physical point of view, it is preferred that the peak value Lp of the output waveform be used for estimation of the peak value ip of the discharge current waveform. Notably, even in the case where the relation is not linear, the peak value ip can be estimated using an approximate characteristic curve. However, the output peak value ip corresponding to the input value of the peak value Lp or the integral value Lq can be obtained on the basis of the above-mentioned relation in the form of a table or by formulating the approximate characteristic curve (providing the output peak value ip corresponding to the input peak value Lp or integral value Lq) and obtaining a function thereof.

Figure 8:
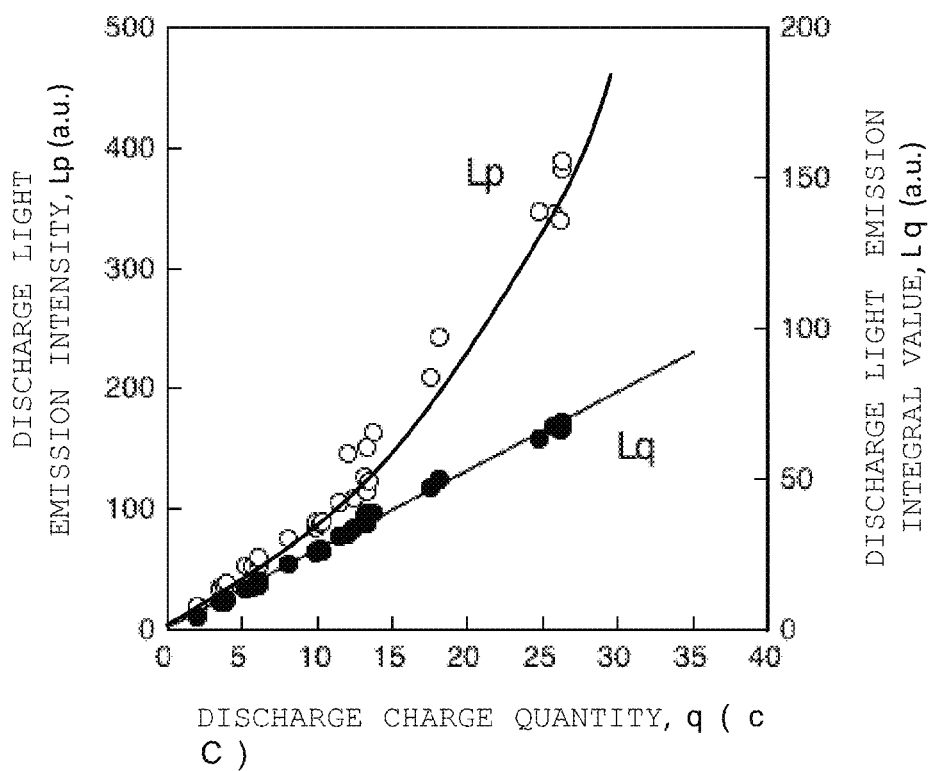
FIG. 8 is a graph used for explaining estimation of the charge quantity q of discharge, wherein plots show actually measured values, and lines show approximate characteristic curves corrected for creation of a database.

Like FIG. 7, FIG. 8 is a graph used for explaining an operation of measuring a light emission signal, such as the peak value Lp of the light emission intensity waveform or the integral value Lq of the light emission intensity, simultaneously with the charge quantity of discharge and estimating the charge quantity q of discharge from the peak value Lp or the integral value Lq on the characteristic curves shown in FIG. 8. In FIG. 8, plots show actually measured values, and lines show approximate characteristic curves corrected for creation of a database. The points on the characteristic curves of this graph are recorded in the database in the form of a table. The relation between the charge quantity q of discharge and the integral value Lq is more linear than the relation between the charge quantity q of discharge and the peak value Lp. Moreover, from the physical point of view, it is preferred that the integral value Lq be used for estimation of the charge quantity q of discharge. Notably, even in the case where the relation is not linear, the charge quantity q of discharge can be estimated using an approximate characteristic curve. However, the output charge quantity q corresponding to the input value of the integral value Lq or the peak value Lp can be obtained on the basis of the above-mentioned relation in the form of a table or by formulating the approximate characteristic curve (providing the output charge quantity q corresponding to the input integral value Lq or peak value Lp) and obtaining a function thereof.

Figure 9:
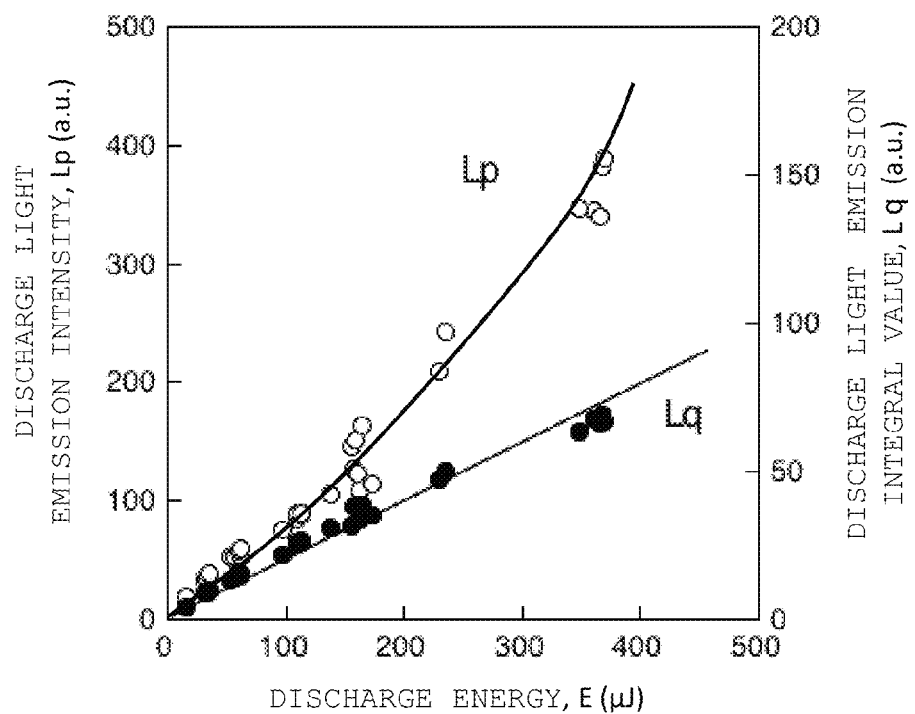
FIG. 9 is a graph used for explaining estimation of discharge energy E, wherein plots show actually measured values, and lines show approximate characteristic curves corrected for creation of a database.

Like FIGS. 7 and 8, FIG. 9 is a graph used for explaining an operation of measuring a light emission signal, such as the peak value Lp of the light emission intensity waveform or the integral value Lq of the light emission intensity, simultaneously with discharge energy and estimating the discharge energy E from the characteristic curves shown in FIG. 9. In FIG. 9, plots show actually measured values, and lines show approximate characteristic curves corrected for creation of a database. The points on the characteristic curves of this graph are recorded in the database in the form of a table. The relation between the discharge energy E and the integral value Lq is more linear than the relation between the discharge energy E and the peak value Lp. Moreover, from the physical point of view, it is preferred that the integral value Lq be used for estimation of the discharge energy E. Notably, even in the case where the relation is not linear, the discharge energy E can be estimated using an approximate characteristic curve. However, the output discharge energy E corresponding to the input value of the peak value Lp or the integral value Lq can be obtained on the basis of the above-mentioned relation in the form of a table or by formulating the approximate characteristic curve (providing the output discharge energy E corresponding to the input peak value Lp or integral value Lq) and obtaining a function thereof.

Figure 10:
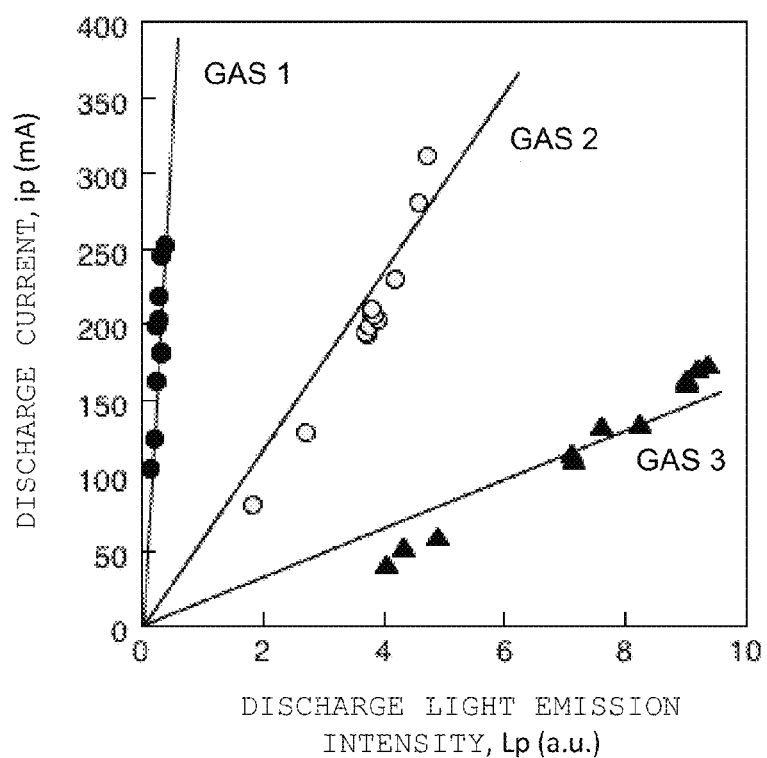
FIG. 10 is a graph used for explaining differences produced among different types of insulation gases.

FIG. 10 is a graph used for explaining differences produced between different types of insulating gases which are examples of different insulation systems. FIG. 10 is a graph showing the relation between the peak value Lp of discharge light emission and the peak value ip of discharge current ip for each of different types of insulating gases. Since the above-described evaluation changes depending on the discharge environment (gas insulation or liquid insulation used), it is necessary to obtain data for each type of insulation gas of interest in advance. Notably, in the present embodiment, the relation between the peak value Lp of discharge light emission and the peak value ip of discharge current ip is shown. However, since the relation between the integral value Lq of discharge light emission and the charge quantity q of discharge or the discharge energy E also changes depending on the discharge environment, it is necessary to obtain data for each insulation system of interest in advance. FIG. 10 shows an example in which the characteristic change depending on the type of the insulation medium (insulation gas in the present example). In the case where the form of discharge changes greatly, data are prepared for each of different discharge forms, which allows more specific evaluation of discharge quantity.

The intensity of an optical signal changes depending on the distance d between the position of light emission and the sensor position (the greater the distance d, the greater the degree to which the intensity of the optical signal drops). Therefore, correction is performed in consideration of this dependency on the distance d. Namely, since the light emission intensity is inverse proportional to the square of the distance d, correction for increasing and decreasing the light emission intensity is performed on the basis of this relation and in consideration of the distance d between the position of light emission and the sensor position.

In the case of a discharge test, the discharge generation portion is an electrode and is known. In contrast, in the case of maintenance diagnosis, since the discharge generation portion is unknown, a position locating technique becomes necessary. In the position locating, since the light emission signal attenuates in inverse proportional to the square of the distance between the generation position and the light receiving element, the data (produced under the assumption that the distance between a generation source and the light receiving element is a predetermined distance) recorded in the database must be subjected to distance correction. Notably, even when distance correction cannot be performed, a relative change in the magnitude of discharge can be evaluated through use of the relation between two values having a linear relation therebetween, such as the relation between the peak value Lp of discharge light emission and the peak value ip of discharge current or the relation between the integral value Lq of discharge light emission and the charge quantity q of discharge.

Although only some exemplary embodiments of this invention have been described in detail above, those skilled in the art will readily appreciated that many modifications are possible in the exemplary embodiments without materially departing from the novel teachings and advantages of this invention. Accordingly, all such modifications are intended to be included within the scope of this invention.

The invention claimed is:

1. A non-contact discharge evaluation method of evaluating discharge of a piece of equipment under measurement in a non-contact manner by optically measuring light emitted as a result of the discharge, the method comprising:
applying a voltage to a discharge source from a known power supply so as to cause the discharge source to emit discharge light, measuring an area of a light intensity waveform which is an integral value of the discharge light emission intensity by using a light receiving element, simultaneously measuring an area of a discharge current waveform which is an integral value of a discharge current value by using a current conversion probe or a current waveform detector, and creating a database in which a relation between analysis data sets obtained by analyzing the waveforms is recorded based on information regarding power applied to the discharge source; and measuring an intensity waveform of discharge light emission from the piece of equipment under measurement by using a light receiving element which is identical to or of the same type as the light receiving element, and comparing light emission data obtained by analyzing the waveform with the data recorded in the database so as to estimate a magnitude of discharge as a value.

2. A non-contact discharge evaluation method according to claim 1, wherein, for each light receiving element used and for a discharge environment produced in each insulation system of interest, the database is created and the magnitude of discharge is estimated.

3. A non-contact discharge evaluation method according to claim 1, wherein the magnitude of discharge is a charge quantity or a discharge energy value which is an integral value of the discharge current.

4. A non-contact discharge evaluation apparatus for evaluating discharge of a piece of equipment under measurement in a non-contact manner by optically measuring light emitted as a result of the discharge, the apparatus comprising:
a database in which a relation between analysis data sets is recorded based on information regarding power applied to a discharge source, the analysis data sets being obtained by an operation of applying a voltage to a discharge source from a known power supply so as to cause the discharge source to emit discharge light, measuring an area of a light intensity waveform which is an integral value of the discharge light emission by using a light receiving element, simultaneously measuring an area of a discharge current waveform which is an integral value of a discharge current value by using a current conversion probe or a current waveform detector, and analyzing the waveforms to obtain the analysis data sets;
a waveform intensity obtaining apparatus which measures an intensity waveform of discharge light emission from the piece of equipment under measurement by using a light receiving element which is identical to or of the same type as the light receiving element, and obtains a waveform intensity thereof;
a waveform analyzing section which analyzes the waveform intensity obtained by the waveform intensity obtaining apparatus;
a comparison section which compares light emission data obtained by analysis in the waveform analyzing section with the data recorded in the database so as to estimate a magnitude of discharge as a value; and
a display section which displays the estimated magnitude of discharge.

5. A non-contact discharge evaluation apparatus according to claim 4, wherein, for each light receiving element used and for a discharge environment produced in each insulation system of interest, the database is created and the magnitude of discharge is estimated.

6. A non-contact discharge evaluation apparatus according to claim 4, wherein the magnitude of discharge is a charge quantity or a discharge energy value which is an integral value of the discharge current.

7. A non-contact discharge evaluation apparatus according to claim 4, wherein the light receiving element is disposed to spatially face the discharge source or is disposed such that the light receiving element is coupled with the discharge source through an optical guide.

8. A non-contact discharge evaluation apparatus according to claim 4, wherein the sensitivity of the light receiving element is increased and decreased in accordance with the light emission intensity by increasing and decreasing the gain of the light receiving element itself or increasing and decreasing a distance between the light receiving element and the light emission source, or the sensitivity of the light receiving element is adjusted by disposing an optical filter or using an optical guide.

9. A non-contact discharge evaluation apparatus according to claim 4, wherein the light receiving element and the waveform intensity obtaining apparatus are disposed in an electromagnetic shield box.

10. A non-contact discharge evaluation apparatus according to claim 4, wherein a plurality of light receiving elements are used, and wiring distances between the light receiving elements and the waveform intensity obtaining apparatus are made equal to one another, or time correction is performed in accordance with length differences thereamong.

11. A non-contact discharge evaluation method of evaluating discharge of a piece of equipment under measurement in a non-contact manner by optically measuring light emitted as a result of the discharge, the method comprising:
applying a voltage to a discharge source from a known power supply so as to cause the discharge source to emit discharge light, measuring an area of a light intensity waveform which is an integral value of the discharge light emission intensity by using a light receiving element and simultaneously measuring an area of a discharge current waveform which is an integral value of a discharge current value by using a current conversion probe or a current waveform detector, analyzing the light intensity waveform to obtain a light intensity waveform analysis data set and analyzing the discharge current waveform to obtain a discharge current waveform analysis data set, and creating a database in which a relation between said light intensity waveform analysis data set and said discharge current waveform analysis data is recorded based on information regarding power applied to the discharge source; and
measuring an intensity waveform of discharge light emission from the piece of equipment under measurement by using a light receiving element which is identical to or of the same type as the light receiving element used to create said database, analyzing said equipment intensity waveform to provide measured equipment light emission data and comparing said measured equipment light emission data with the data recorded in the database to provide an estimate a magnitude of discharge as a value.

12. A non-contact discharge evaluation method according to claim 11, wherein, for each light receiving element used and for a discharge environment produced in each insulation system of interest, the database is created and the magnitude of discharge is estimated.

13. A non-contact discharge evaluation method according to claim 11, wherein the magnitude of discharge is a charge quantity or a discharge energy value which is an integral value of the discharge current.

* * * * *